United States Patent
Verheesen et al.

(10) Patent No.: US 9,516,879 B2
(45) Date of Patent: Dec. 13, 2016

(54) CHITINOUS POLYSACCHARIDE ANTIGEN-BINDING PROTEINS

(75) Inventors: Peter Verheesen, Mariakerke (BE); Chris De Jonghe, Aartselaar (BE); Erik Jongedijk, Lokeren (BE)

(73) Assignee: Agrosavfe N.V., Ghent (BE)

( * ) Notice: Subject to any disclaimer, the term of this patent is extended or adjusted under 35 U.S.C. 154(b) by 587 days.

(21) Appl. No.: 13/819,330

(22) PCT Filed: Aug. 26, 2011

(86) PCT No.: PCT/EP2011/064734
§ 371 (c)(1),
(2), (4) Date: May 11, 2013

(87) PCT Pub. No.: WO2012/025619
PCT Pub. Date: Mar. 1, 2012

(65) Prior Publication Data
US 2013/0227747 A1    Aug. 29, 2013

Related U.S. Application Data

(60) Provisional application No. 61/402,307, filed on Aug. 26, 2010.

(30) Foreign Application Priority Data

Sep. 7, 2010 (EP) .................................... 10175543

(51) Int. Cl.
| | |
|---|---|
| C07K 16/00 | (2006.01) |
| A61K 39/00 | (2006.01) |
| A01N 37/46 | (2006.01) |
| C07K 16/16 | (2006.01) |
| C07K 16/18 | (2006.01) |
| A01G 1/00 | (2006.01) |
| G01N 33/569 | (2006.01) |
| C07K 16/14 | (2006.01) |

(52) U.S. Cl.
CPC ............ *A01N 37/46* (2013.01); *A01G 1/001* (2013.01); *C07K 16/14* (2013.01); *C07K 16/16* (2013.01); *C07K 16/18* (2013.01); *G01N 33/56961* (2013.01); *C07K 2317/22* (2013.01); *C07K 2317/569* (2013.01)

(58) Field of Classification Search
CPC ................................................... A01N 37/46
See application file for complete search history.

(56) References Cited

U.S. PATENT DOCUMENTS

| | | |
|---|---|---|
| 2,651,883 A | 9/1953 | Hedrick et al. |
| 3,316,676 A | 5/1967 | Legal, Jr. et al. |
| 3,598,565 A | 8/1971 | Graves |
| 3,707,807 A | 1/1973 | Graves |
| 4,245,432 A | 1/1981 | Dannelly |
| 5,004,699 A * | 4/1991 | Winters ...................... 435/7.31 |
| 5,876,739 A | 3/1999 | Turnblad et al. |
| 6,180,141 B1 | 1/2001 | Lemercier et al. |
| 6,228,599 B1 | 5/2001 | Knox |
| 7,494,526 B2 | 2/2009 | Yavitz |
| 8,598,081 B2 | 12/2013 | Jongedijk et al. |
| 2004/0192645 A1* | 9/2004 | Hollingsworth ..... A61K 49/006 514/55 |
| 2005/0107256 A1 | 5/2005 | Barnwell et al. |
| 2011/0136255 A1* | 6/2011 | Dotan ................ G01N 33/6854 436/501 |

FOREIGN PATENT DOCUMENTS

| | | |
|---|---|---|
| WO | 90/06954 A1 | 6/1990 |
| WO | 9217786 A1 | 10/1992 |
| WO | 9404673 | 3/1994 |
| WO | 9411511 A1 | 5/1994 |
| WO | 9825445 | 6/1998 |
| WO | 9937681 | 7/1999 |
| WO | 0024884 | 5/2000 |
| WO | 0043507 | 7/2000 |
| WO | 0140310 | 6/2001 |
| WO | 0190190 | 11/2001 |
| WO | 02085945 | 10/2002 |
| WO | 03025020 | 3/2003 |
| WO | 03031477 | 4/2003 |
| WO | 03035694 | 5/2003 |
| WO | 03074660 A2 | 9/2003 |
| WO | 2004004453 | 1/2004 |
| WO | 2004031379 A1 | 4/2004 |
| WO | 2005001098 | 1/2005 |
| WO | 2005102045 | 11/2005 |
| WO | 2006112700 | 10/2006 |
| WO | 2007049794 | 3/2007 |
| WO | 2007103075 | 9/2007 |
| WO | 2007118670 | 10/2007 |
| WO | 2010066740 | 6/2010 |
| WO | 2010107312 | 9/2010 |
| WO | 2011/124612 A1 | 10/2011 |
| WO | 2012/025619 | 3/2012 |
| WO | 2012025621 | 3/2012 |
| WO | WO/2012/025619 | 3/2012 |

OTHER PUBLICATIONS

Agdour, Siham et al., Production and characterization of the recombinant wheat chitinase Wch1 and generation of chitin-specific antibodies, Master of Science, dated Aug. 31, 2007.

(Continued)

*Primary Examiner* — Albert Navarro
(74) *Attorney, Agent, or Firm* — TraskBritt, P.C.

(57) ABSTRACT

Described is an antigen-binding protein, preferably comprising an amino acid sequence that comprises four framework regions and three complementarity-determining regions, wherein the antigen-binding protein is capable of binding a chitinous polysaccharide, and uses thereof.

21 Claims, No Drawings

(56) References Cited

OTHER PUBLICATIONS

Joshi, Mohan Chandra et al., An Insecticidal GroEL Protein with Chitin Binding Activity from *Xenorhabdus nematophila*, The Journal of Biological Chemistry, Oct. 17, 2008, pp. 28287-28296, Vol. 283, No. 42.

Secundino, N. F C et al., *Lutzomyia longipalpis* Peritrophic Matrix: Formation, Structure, and Chemical Composition, Journal of Medical Entomology, 2005, pp. 928-938, vol. 42, No. 6.

Janeway et al., Immunobiology, 3rd edition, 1997, Garland Publishing Inc. New York, pp. 3:1-3:11.

Rudikoff et al., Proc Natl Sci US A. Mar. 1982;79(6):1979-83.

Ewert et al., Biochemistry. Mar. 19, 2001; 41 (11):3528-36.

Casero et al.; The monoclonal antibody JIM5 indicates patterns of pectin deposition in relation to pit fields at the plasma-membrane-face of tomato pericarp cell walls; Protoplasma; vol. 188, No. 1-2; 1995; pp. 133-137.

Pattathil et al.; A Comprehensive Toolkit of Plant Cell Wall Glycan-Directed Monoclonal Antibodies; Plant Physiology; vol. 153; No. 2; Jun. 2010; pp. 514-525.

International Search Report PCT/EP2011/064740 dated Dec. 12, 2011.

Pattathil et al.; Supplemental Materials: A Comprehensive Toolkit of Plant Cell Wall Glycan-Directed Monoclonal Antibodies; Plant Physiology; Jun. 2010; pp. 1-17.

Van Der Linden et al.; Comparison of physical chemical properties of llama VHH antibody fragments and mouse monoclonal antibodies; Biochimica el Biophysica Acta, Protein Structure and Molecular Enzymology; vol. 1431, No. 1, Apr. 12, 1999, pp. 37-46.

Stijlemans B et al.; "Efficient targeting of conserved cryptic epitopes of infectious agents by single domain antibodies. African trypanosomes as paradigm", Journal of Biological Chemistry, American Society for Biochemistry and Molecular Biology, Inc., vol. 279, No. 2, pp. 1256-1261, Mar. 10, 2003.

Muyldermans et al., Camelid immunoglobulins and nanobody technology, Veterinary Immunology and Immunopathology, 2009, pp. 178-183, vol. 128.

Willats et al., In-situ analysis of pectic polysaccharides in seed mucilage and at the roof surface of Arabidopsis thaliana, Planta, 2001, pp. 37-44, vol. 213, Springer-Verlag.

De Hoff et al., Mol Genet Genomics, Jul. 2009, pp. 1-15, vol. 282. doi:10.1007/s00438-009-0460-8. Epub Jun. 2, 2009.

Knox, JP FASEB J. Aug. 1995, pp. 1004-1012, vol. 9, No. 11.

\* cited by examiner

SEQUENCE LISTING

```
<160> NUMBER OF SEQ ID NOS: 11

<210> SEQ ID NO 1
<211> LENGTH: 122
<212> TYPE: PRT
<213> ORGANISM: Lama glama
<220> FEATURE:
<221> NAME/KEY: MISC_FEATURE
<223> OTHER INFORMATION: 15A9
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
```

```
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(111)
<223> OTHER INFORMATION: CDR3
<220> FEATURE:
<221> NAME/KEY: MISC_FEATURE
<222> LOCATION: (112)..(122)
<223> OTHER INFORMATION: FR4

<400> SEQUENCE: 1
```

Gln Val Gln Leu Gln Glu Ser Gly Gly Gly Leu Val Gln Pro Gly Gly
1               5                   10                  15

Ser Leu Arg Leu Ser Cys Val Ala Ala Arg Thr Ile Phe Ser Ser Tyr
            20                  25                  30

Ile Met Gly Trp Phe Arg Gln Ala Pro Gly Lys Glu Arg Glu Phe Val
        35                  40                  45

Ala Arg Ile Trp Trp Ser Gly Asp Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Ser Met Asn Ser Leu Lys Pro Glu Asp Thr Ala Val Tyr Tyr Cys
                85                  90                  95

Ala Ala Ser Pro Tyr Tyr Ser Ser Asp Gln Ser Gln Tyr Asn Tyr Trp
            100                 105                 110

Gly Gln Gly Thr Gln Val Thr Val Ser Ser
        115                 120

```
<210> SEQ ID NO 2
<211> LENGTH: 130
<212> TYPE: PRT
<213> ORGANISM: Lama glama
<220> FEATURE:
<221> NAME/KEY: MISC_FEATURE
<223> OTHER INFORMATION: 15D1
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(119)
<223> OTHER INFORMATION: CDR3
<220> FEATURE:
<221> NAME/KEY: MISC_FEATURE
<222> LOCATION: (120)..(130)
<223> OTHER INFORMATION: FR4

<400> SEQUENCE: 2
```

Gln Val Gln Leu Gln Glu Ser Gly Gly Gly Leu Val Gln Pro Gly Gly
1               5                   10                  15

-continued

```
Ser Leu Arg Leu Ser Cys Ala Ala Ser Gly Phe Phe Leu Glu Tyr Tyr
            20                  25                  30

Asp Ile Gly Trp Phe Arg Gln Ala Pro Gly Glu Glu Arg Glu Gly Val
            35                  40                  45

Ser Cys Leu Ser Ala Tyr Gly His Met Pro Arg Tyr Ala Asp Ala Val
    50                  55                  60

Lys Gly Arg Phe Thr Ile Ser Arg Asp Asn Lys Asn Thr Val Tyr
65                  70                  75                  80

Leu Gln Met Asn Ser Leu Lys Pro Asp Asp Thr Ala Ile Tyr Tyr Cys
                85                  90                  95

Ala Arg Asn Cys Tyr Thr Thr Thr Gly His Gly Gly Thr Val Ile Arg
                100                 105                 110

Ser Ser Thr Ser Ser Thr Ser Trp Gly Gln Gly Thr Gln Val Thr Val
            115                 120                 125

Ser Ser
    130

<210> SEQ ID NO 3
<211> LENGTH: 130
<212> TYPE: PRT
<213> ORGANISM: Lama glama
<220> FEATURE:
<221> NAME/KEY: MISC_FEATURE
<223> OTHER INFORMATION: 15E4
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(119)
<223> OTHER INFORMATION: CDR3
<220> FEATURE:
<221> NAME/KEY: MISC_FEATURE
<222> LOCATION: (120)..(130)
<223> OTHER INFORMATION: FR4

<400> SEQUENCE: 3

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Phe Leu Glu Tyr Tyr
            20                  25                  30

Asp Ile Gly Trp Phe Arg Gln Ala Pro Gly Glu Glu Arg Glu Gly Val
            35                  40                  45

Ser Cys Leu Ser Ala Tyr Gly His Met Pro Arg Tyr Ala Asp Ala Val
    50                  55                  60

Lys Gly Arg Phe Thr Met Ser Arg Asp Asn Asn Lys Asn Thr Val Tyr
65                  70                  75                  80
```

Leu Gln Met Asn Ser Leu Lys Pro Asp Asp Thr Ala Ile Tyr Tyr Cys
                85                  90                  95

Ala Arg Asn Cys Tyr Thr Thr Thr Gly His Gly Gly Thr Val Ile Arg
            100                 105                 110

Ser Ser Thr Ser Ser Thr Ser Trp Gly Gln Gly Thr Gln Val Thr Val
        115                 120                 125

Ser Ser
    130

<210> SEQ ID NO 4
<211> LENGTH: 130
<212> TYPE: PRT
<213> ORGANISM: Lama glama
<220> FEATURE:
<221> NAME/KEY: MISC_FEATURE
<223> OTHER INFORMATION: 15G2
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(119)
<223> OTHER INFORMATION: CDR3
<220> FEATURE:
<221> NAME/KEY: MISC_FEATURE
<222> LOCATION: (120)..(130)
<223> OTHER INFORMATION: FR4

<400> SEQUENCE: 4

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Phe Leu Glu Tyr Tyr
            20                  25                  30

Asp Ile Gly Trp Phe Arg Gln Ala Pro Gly Glu Glu Arg Glu Gly Val
        35                  40                  45

Ser Cys Leu Ser Ala Tyr Gly His Met Pro Arg Tyr Ala Asp Ala Val
    50                  55                  60

Lys Gly Arg Phe Thr Met Ser Arg Asp Asn Lys Asn Thr Val Tyr
65                  70                  75                  80

Leu Gln Met Asn Ser Leu Lys Pro Asp Asp Thr Ala Ile Tyr Tyr Cys
                85                  90                  95

Ala Arg Asn Cys Tyr Thr Thr Thr Gly His Gly Gly Thr Val Ile Arg
            100                 105                 110

Ser Ser Thr Ser Ser Thr Ser Trp Gly Gln Gly Thr Gln Val Thr Val
        115                 120                 125

Ser Ser
    130

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
gtcctggctg ctcttctaca agg                               23

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
cctggctgct cttctacaag gtg                               23

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
ggtacgtgct gttgaactgt tcc                               23

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
gatgtgcagc tgcaggagtc tggrggagg                         29

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
ggactagtgc ggccgctgga gacggtgacc tgggt                  35

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ttatgcttcc ggctcgtatg                                   20

<210> SEQ ID NO 11
<211> LENGTH: 19
<212> TYPE: DNA
<213> ORGANISM: Artificial Sequence
<220> FEATURE:
<223> OTHER INFORMATION: Primer -continued

```
<400> SEQUENCE: 11
ccacagacag ccctcatag                                                    19
```

CHITINOUS POLYSACCHARIDE ANTIGEN-BINDING PROTEINS

CROSS-REFERENCE TO RELATED APPLICATIONS

This application is a national phase entry under 35 U.S.C. §371 of International Patent Application PCT/EP2011/064734, filed Aug. 26, 2011, designating the United States of America and published in English as International Patent Publication WO 2012/025619 A1 on Mar. 1, 2012, which claims the benefit under Article 8 of the Patent Cooperation Treaty and under 35 U.S.C. §119(e) to U.S. Provisional Patent Application Ser. No. 61/402,307, filed Aug. 26, 2010, and to European Patent Application Serial No. 10175543.7, filed Sep. 7, 2010.

TECHNICAL FIELD

The present invention relates to an antigen-binding protein, preferably comprising an amino acid sequence that comprises four framework regions and three complementarity-determining regions, wherein the antigen-binding protein is capable of binding a chitinous polysaccharide, and uses thereof.

BACKGROUND

Polysaccharides are polymeric carbohydrate structures, formed of repeating units of monosaccharides, joined together by glycosidic bonds. Depending on their chemical composition, polysaccharides are further divided into polysaccharides sensu strictu, which contain only hydroxyl and acetyl groups and aminopolysaccharides, which contain also nitrogen (amino or amido-groups). Natural aminopolysaccharides include chitin and chitosan (only containing hydroxyl, amino and acetyl groups) and keratin sulphate, hyaluronic acid, chondroitin, dermatan sulphates and heparin, which contain also carboxyl and sulphate groups.

Chitin is the most abundant natural aminopolysaccharide and is widely distributed amongst invertebrates including arthropods, nematodes, crustaceans, fungi and some protozoa. Chitin is a polymer of N-acetyl-D-glucosamine. The major form of chitin is α-chitin, as encountered in fungi and arthropods and is characterized by an anti-parallel joining of the polysaccharide chains. The β-form, in which the chains are joined in a parallel way, is rather rare and is found in diatoms and some protists. Chitosan is the N-deacetylated derivative of chitin, although this N-deacetylation is almost never complete. Chitin and chitosan correspond to a family of polymers varying in acetyl content, wherein the degree of acetylation determines whether the aminopolysaccharide is named chitin (degree of acetylation >70%) or chitosan (degree of acetylation <70%).

Chitin is the second most abundant biopolymer in nature after cellulose and, together with its derivatives, it has applications in a wide variety of fields, including medical, pharmaceutical, cosmetics, biotechnology, food industry, agriculture and environmental protection. Despite its huge annual production, chitin still remains an underutilized biomass resource, primarily because of its intractable bulk structure. Therefore, the determination of the concentration of chitinous polysaccharides, as well as the identification of their structure and possible modifications is extremely important, especially for efficient industrial processing. Moreover, it may be important to target specific chitinous polysaccharides, for removal out of the matrix or for modification of their structure.

Special attention has been paid to chitin-binding proteins for detection and purification applications. Chitin-binding proteins are rather common and form a highly diverse group, including but not limited to chitinases, hydrolyzing the internal β-1,4-glycosidic linkages of chitin. Chitin-binding proteins have been detected in bacteria (Folders et al., 2000; Joshi et al., 2008), plants (Iseli et al., 1993), invertebrates (Suetake et al, 2000) and vertebrates (Boot et al., 1995). Chitin-binding proteins are characterized by one or more chitin-binding domains; these binding domains may or may not be linked to a catalytic domain. The binding domains can be isolated and fused to other polypeptides, to create novel chitin-binding proteins.

Chitin-binding domains and chitin-binding proteins do have multiple possible applications: as chitin is absent in vertebrates and plants, chitin-binding domains can be used to detect infection or contamination by chitin-containing organisms, as disclosed in WO 9217786 or WO 2005005955. By fusing a chitin-binding domain to a protein of interest, the protein of interest can be purified on a chitin carrier, using affinity chromatography. Moreover, WO 9411511 discloses biocidal chitin-binding proteins that exert an antifungal activity and can be used as anti-microbial agent. Joshi et al. (2008) describe a chitin-binding protein with insecticidal activity.

However, notwithstanding their possible value, the use of the chitin-binding domains and chitin-binding proteins is rather limited, due to several drawbacks. Most of the chitin-binding domains show cross reactivity with other polysaccharides, limiting the value of the binding domain for specific detection of chitin (Itoh et al., 2002; Guillen et al., 2010). Several chitin-binding domains bind chitin with rather low affinity (Neeraja et al., 2010b), limiting the applications in all fields. Moreover, chitin-binding domains may bind chitin in an irreversible way (Xu et al., 2000; WO 03074660), complicating the use in affinity purification, because the protein cannot be eluted under non-denaturing conditions.

To solve the problems, the introduction of mutations in the chitin-binding domains has been proposed to modulate the chitin-binding activity and to create modified chitin-binding domains with reversible binding properties (Ferrandon et al., 2003; WO 03074660). However, there is still a need for better chitin-binding proteins.

Antibodies are known for their high affinity and specificity. However, production of antibodies against polysaccharides is far from evident, as polysaccharides are hardly immunogenic. Anti-chitin IgA type antibodies have been detected in serum of Crohn's disease, ulcerative colitis and inflammatory bowel disease (WO 2009069007; Dotan et al., 2006; Seow et al., 2008; Seow et al., 2009) and after *Candida albicans* infection (Sendid et al., 2008). Sales et al. (2001) and Martin et al. (2007) describe the generation of polyclonal rabbit anti-chitin antibodies; U.S. Pat. No. 5,004,699 discloses the use of a mouse serum containing polyclonal anti-chitin antibodies for the detection of fungi and yeasts. However, for the intended uses, monoclonal antibodies, and preferably single chain antibodies are needed. Anti-chitin single chain antibodies have not been disclosed in the art.

WO 94004678 describes immunoglobulins devoid of light chains. It is demonstrated that such antigen-binding proteins comprising an amino acid sequence that comprises four framework regions (FR) and three complementarity-determining regions (CDR), and more specifically VHH, display superior characteristics over monoclonal antibodies as they are extremely stable and retain binding capacity to the target antigen under high temperature (van der Linden et al., 1999), or denaturing conditions (Dolk et al., 2005) and are resistant to harsh regenerating conditions (Saerens et al., 2005). Therefore, the antigen-binding proteins are particularly well suited to be used in industrial processes. However, up to now, such antigen-binding proteins capable of binding polysaccharide are not described, although attempts to make such anti-bodies have been made. Indeed, WO 94004678 disclosed camelid antibodies against carbohydrates, but those are directed against the variant surface antigen of *Trypanosoma evansi*, which is a glycoprotein. WO 94004678 is neither disclosing nor suggesting antibodies against polysaccharides sensu strictu, or against aminopolysaccharides. Moreover, when De Simone et al. (2008) analyze the immune response in llamas immunized with different types of antigens, i.e., protein, conjugated hapten or polysaccharide (dextran sulphate), no anti-dextran immune response could be detected in the immunized animals, in contrast to clear immune responses to the protein and conjugated hapten antigens; whereas it is relatively easy to generate classical anti-dextran antibodies (Cisar et al., 1975; Bona, 1993). The lack of antibody response in the immunoglobulins devoid of light chains is not unexpected: indeed anti-polysaccharide responses in humans are clearly dominated by IgM and IgG1 types (Bona, 1993) whereas heavy chain antibodies from camelids belong to the IgG2 and IgG3 classes (Hamers-Casterman et al., 1993; Daley et al., 2010). Moreover, it is known that interactions between polysaccharides and individual binding sites in a protein are typically weak and binding strength and specificity is enhanced through polymeric interactions between polysaccharides and oligomeric polysaccharide-binding proteins (Mammen et al., 1998). Being strictly monomeric binders by nature (Muyldermans et al., 2001), VHH are in this respect not well suited to bind polysaccharides. Therefore, the person skilled in the art would assume that it is extremely difficult, if not impossible to raise immunoglobulins devoid of light chains against chitinous polysaccharides. Another complicating factor is the low water-solubility of chitinous polysaccharides, particularly chitin, which means that many standard techniques used for isolating antibodies that are carried out in aqueous solution, cannot be applied.

To obtain and isolate antigen-binding proteins specific for chitinous polysaccharides, an original and innovative approach was used. By immunizing llamas with a complex mixture containing chitinous polysaccharides, rather than with a purified antigen, followed by selecting antigen-binding proteins using immobilized solubilized chitin and finally screening with chitin, prepared directly on a solid surface, we were capable of isolating antigen-binding proteins, more specifically, antigen-binding proteins comprising an amino acid sequence that comprises four framework regions (FR) and three complementarity-determining regions (CDR), wherein the antigen-binding proteins are capable to bind chitinous polysaccharides. Preferably, the antigen-binding proteins are binding to chitin.

DISCLOSURE

A first aspect hereof is an antigen-binding protein capable of binding a chitinous polysaccharide.

An "antigen-binding protein" as used herein, means the whole or part of a proteinaceous (protein, protein-like or protein-containing) molecule that is capable of binding using specific intermolecular interactions to a target molecule. An antigen-binding protein can be a naturally occurring molecule, it can be derived from a naturally occurring molecule, or it can be entirely artificially designed. An antigen-binding protein can be immunoglobulin-based or it can be based on domains present in proteins, including but not limited to microbial proteins, protease inhibitors, toxins, fibronectin, lipocalins, single chain antiparallel coiled coil proteins or repeat motif proteins. Non-limiting examples of such antigen-binding proteins are carbohydrate antigen-binding proteins (CBD) (Blake et al., 2006), heavy chain antibodies (hcAb), single domain antibodies (sdAb), minibodies (Tramontano et al., 1994), the variable domain of camelid heavy chain antibodies (VHH), the variable domain of the new antigen receptors (VNAR), affibodies (Nygren et al., 2008), alphabodies (WO 2010066740), designed ankyrin-repeat domains (DARPins) (Stumpp et al., 2008), anticalins (Skerra et al., 2008), knottins (Kolmar et al., 2008) and engineered CH2 domains (nanoantibodies; Dimitrov, 2009).

"Polysaccharides" as used herein are polymeric carbohydrate structures, formed of repeating units of monosaccharides, joined together by glycosidic bonds, including aminopolysaccharides, and derivatives thereof. "Aminopolysaccharides," as used herein, means nitrogen (amido or amino-groups) containing polysaccharides, but it excludes polysaccharides further containing carboxyl- or sulphate-groups. Preferably, the polysaccharides are not contaminated with other non-polysaccharide compounds, and have a purity of at least 85% w/w, preferably 90% w/w, more preferably 95% w/w, even more preferably 98% w/w, most preferably 99% w/w. Polysaccharides are distinct from oligosaccharides by their size, complexity and degree of polymerization. Polysaccharides as used here comprise at least ten monosaccharides units, preferably at least fifteen monosaccharide units.

"Chitinous polysaccharides," as used herein, means aminopolysaccharides and derivatives or modifications thereof, including but not limited to nitration, phosphorylation, sulphation, acylation, deacetylation, hydroxyalkylation, alkylation and/or graft copolymerization. Preferably, the chitinous polysaccharide is a natural aminopolysaccharide.

"Capable of binding to a chitinous polysaccharide" as used herein, means that the antigen-binding protein can form a stable complex with a chitinous polysaccharide, preferably an insoluble chitinous polysaccharide, wherein the efficacy of the binding can be evaluated by precipitating the chitinous polysaccharide/protein complex, similar to described by Folders et al. (2000). Alternatively, chitinous polysaccharides may be immobilized on an insoluble carrier to allow recruitment of the antigen-binding protein and evaluation of the binding.

Preferably, the antigen-binding proteins hereof are monoclonal antigen-binding proteins. A "monoclonal antigen-binding protein" as used herein means an antigen-binding protein produced by a single clone of cells and therefore a single pure homogeneous type of antigen-binding protein. More preferably, the antigen-binding proteins hereof consist of a single polypeptide chain. Most preferably, the antigen-binding proteins hereof comprise an amino acid sequence that comprises four framework regions and three complementarity-determining regions, or any suitable fragment thereof, and confer their binding specificity to the chitinous polysaccharide by the amino acid sequence of three complementarity-determining regions or CDRs, each non-contiguous with the others (termed CDR1, CDR2, CDR3), which are interspersed amongst four framework regions or FRs, each non-contiguous with the others (termed FR1, FR2, FR3, FR4), preferably in a sequence FR1-CDR1-FR2-CDR2-FR3-CDR3-FR4). The delineation of the FR and CDR sequences is based on the unique numbering system according to Kabat. The antigen-binding proteins comprising an amino acid sequence that comprises four framework regions and three complementarity-determining regions, are known to the person skilled in the art and have been described, as a non-limiting example in Wesolowski et al. (2009). The length of the CDR3 loop is strongly variable and can vary from 0, preferably from 1, to more than 20 amino acid residues, preferably up to 25 amino acid residues.

Preferably, the antigen-binding protein hereof is easy to produce at high yield, preferably in a microbial recombinant expression system, and convenient to isolate and/or purify subsequently. Also preferably, the antigen-binding protein is stable, both during storage and during utilization, meaning that the integrity of the antigen-binding protein is maintained under storage and/or utilization conditions, which may include elevated temperatures, freeze-thaw cycles, changes in pH or in ionic strength, UV-irradiation, presence of harmful chemicals and the like. More preferably, the antigen-binding protein is stable in an agrochemical formulation as further defined. Most preferably, the antigen-binding protein remains stable in an agrochemical formulation (as further defined) when stored at ambient temperature for a period of up to two years or when stored at 54° C. for a period of at least two weeks.

Binding of the antigen-binding protein to a chitinous polysaccharide occurs preferably with high affinity: typically, the dissociation constant of the binding between the antigen-binding protein and the chitinous polysaccharide target molecule is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M. Preferably, binding of the antigen-binding protein to the chitinous polysaccharide is specific, meaning that the antigen-binding protein preferentially binds to a chitinous polysaccharide that is present in a homogeneous or heterogeneous mixture of different polysaccharides or other components. Specificity of binding of an antigen-binding protein can be analyzed by methods such as ELISA, as described in Example 3, in which the binding of the antigen-binding protein to its target molecule is compared with the binding of the antigen-binding protein to an unrelated molecule and with a specific sticking of the antigen-binding protein to the reaction vessel. In certain embodiments, a specific binding interaction will discriminate between desirable and undesirable antigens in a sample, in some embodiments more than about ten- to 100-fold or more (e.g., more than about 1000- or 10,000-fold). Preferably, the binding of the antigen-binding protein to its target molecule is still functional under harsh conditions, such as low or high temperature, low or high pH, low or high ionic strength, UV-irradiation, presence of denaturing chemicals or the like. In one preferred embodiment, the harsh conditions are defined by a pH range from 4 to 9, more preferably by a pH range from 3 to 10, even more preferably by a pH range from 2 to 10, most preferably by a pH range from 1 to 11. In another preferred embodiment, the harsh conditions are defined by a temperature range from 4-50° C., more preferably, a temperature range from 0-55° C., even more preferably, a temperature range from 0-60° C. In still another preferred embodiment, the harsh conditions are defined as conditions prevalent in an agrochemical formulation as further defined.

In one preferred embodiment, the chitinous polysaccharide is chitin. "Chitin" as used herein means a natural aminopolysaccharide consisting of a long chain of N-acetylglucosamine, with a degree of deacetylation, which is lower than 70%. It is the main component of the cell walls of fungi, and is also present in the bud scars of *Saccharomyces* yeasts as well as the exoskeletons of arthropods such as crustaceans (e.g., lobsters and shrimps) and insects.

In one preferred embodiment, the chitinous polysaccharide, preferably the chitin, is comprised in a solid surface, such as a chitin paramagnetic bead or immobilized onto a solid surface, such as solubilized chitin, which is immobilized on an immunosorbent multi-well plate surface as non-limiting examples.

In another preferred embodiment, the chitinous polysaccharide, preferably the chitin, is comprised in or derived from an arthropod, preferably from an insect. "Comprised in" as used herein, means contained in, located in or enclosed in an arthropod, preferably an insect, or any particular part or structure thereof, such as the gut of an insect as a non-limiting example; "derived from," as used herein means prepared from, produced from or isolated from an arthropod, preferably an insect, or any particular part or structure thereof, such as the shell of a crab or the exoskeleton of an insect as non-limiting examples. Preferably, the insect is considered as a pest insect. A "pest insect," as used herein, is an insect that is detrimental to humans or human concerns, and includes, but is not limited to agricultural pest organisms, including but not limited to aphids, grasshoppers, caterpillars, beetles, etc., household pest organisms, such as cockroaches, ants, etc., and disease vectors, such as malaria mosquitoes.

In still another preferred embodiment, the chitinous polysaccharide, preferably the chitin, is comprised in or derived from a fungus, including but not limited to filamentous fungi and yeasts. "Comprised in" as used herein, means contained in, located in or enclosed in a fungus or a yeast, or any particular part or structure thereof, such as the hyphae of the fungus or the bud scars of a yeast as a non-limiting example; "derived from," as used herein, means prepared from, produced from or isolated from a fungus or a yeast, or any particular part or structure thereof, such as the spores of a fungus or the cell wall of a yeast as non-limiting examples. Preferably, the fungus is considered as a fungal disease organism. A "fungal disease organism," as used herein, is a fungal organism that is detrimental to humans or human concerns, and includes, but is not limited to agricultural fungal diseases, including but not limited to blights, smuts, molds, etc., animal and human fungal diseases, including but not limited to *Candida albicans* infections.

In yet another preferred embodiment, the antigen-binding protein binding to a chitinous polysaccharide, preferably to chitin, has an insecticidal activity. "Insecticidal activity," as used herein, means that the antigen-binding protein is capable of either killing the insect, preferably the pest insect, or is capable of slowing or inhibiting the growth, the reproduction and/or the detrimental activity (such as the feeding on a crop) of the insect, preferably the pest insect. The insecticidal activity of an antigen-binding protein hereof can be determined by feeding the insect with the antigen-binding protein hereof and by monitoring the insect survival, the reproduction rate and/or the result of the detrimental activity (such as the amount of crop leaves that is eaten by the insect). By way of a non-limiting example, the antigen-binding protein hereof can by binding to chitin, lining the insect's gut, interfere with the digestive system of the insect and as such slow down or completely impair feeding of the insect, which may ultimately lead to starvation.

In still another preferred embodiment, the antigen-binding protein binding to a chitinous polysaccharide, preferably to chitin, has a fungicidal activity. "Fungicidal activity," as used herein, means that the antigen-binding protein is capable of either partially or completely inhibiting the growth of a fungus or of killing the fungus, preferably the fungal disease organism, as described above. The fungicidal activity of an antigen-binding protein hereof can be determined by adding the antigen-binding protein hereof to the culture medium of a fungus or yeast and by monitoring the fungal growth rates and survival, using any of the methods as described in WO 9411511.

Preferably, the antigen-binding proteins hereof are derived from camelid antibodies, preferably from heavy chain camelid antibodies, devoid of light chains, such as variable domains of heavy chain camelid antibodies (VHH). Preferably, the VHH comprises, preferably consists of a sequence selected from the group consisting of SEQ ID NO:1 through SEQ ID NO:4 or homologues thereof. Homologues, as used here are sequences wherein each framework region and each complementarity-determining region shows at least 80% identity, preferably at least 85% identity, more preferably 90% identity, even more preferably 95% identity with the corresponding region in the reference sequence (i.e., FR1homologue versus FR1reference, CDR1homologue versus CDR1reference, FR2h versus FR2r, CDR2h versus CDR2r, FR3h versus FR3r, CDR3h versus CDR3r and FR4h versus FR4r) as measured in a BLASTp alignment (Altschul et al., 1997; FR and CDR definitions according to Kabat).

In still another embodiment, a nucleic acid sequence encoding any of the above antigen-binding proteins or functional fragments thereof is also part of the present invention. The invention also encompasses the use of any antigen-binding protein hereof to isolate amino acid sequences that are responsible for specific binding to a chitinous polysaccharide, preferably chitin, to construct artificial binding domains based on the amino acid sequences. Indeed, in the antigen-binding proteins hereof, the framework regions and the complementarity-determining regions are known, and the study of derivatives of the antigen-binding proteins, binding to the same chitinous polysaccharide, will allow deducing the essential amino acids involved in binding the chitinous polysaccharide. This knowledge can be used to construct a minimal antigen-binding protein and to create derivatives thereof.

Further, the present invention also envisages expression vectors comprising nucleic acid sequences encoding any of the above antigen-binding proteins or functional fragments thereof, as well as host cells expressing such expression vectors. Suitable expression systems include constitutive and inducible expression systems in bacteria or yeasts, virus expression systems, such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris*, and the like. Suitable animal host cells include HEK 293, COS, S2, CHO, NS0, DT40 and the like. The cloning, expression and/or purification of the antigen-binding proteins can be done according to techniques known by the person skilled in the art. Accordingly, the invention encompasses methods of manufacturing antigen-binding proteins hereof, the method comprising the following steps:

(i) Cloning the nucleic acid sequences encoding any of the antigen-binding proteins hereof or functional fragments thereof in a suitable expression vectors, and
(ii) Expressing the antigen-binding proteins in a suitable expression host; and
(iii) Isolating and/or purifying the antigen-binding proteins from the lysate or supernatant of the expression host.

Although naive or synthetic libraries of VHH (for examples of such libraries, see WO 9937681, WO 0043507, WO 0190190, WO 03025020 and WO 03035694) may contain suitable binders against chitinous polysaccharides, one embodiment of this invention includes the immunization of an individual of a species of Camelidae with one or a combination of several chitinous polysaccharides, to expose the immune system of the animal to the chitinous polysaccharides. Thus, as further described herein, such VHH sequences can preferably be generated or obtained by suitably immunizing a species of Camelidae with one or a combination of several chitinous polysaccharides, by obtaining a suitable biological sample from the Camelidae species (such as a blood sample, or any sample of B-cells), and by generating $V_HH$ sequences directed against the desired chitinous polysaccharide, starting from the sample. Such techniques will be clear to the skilled person. Yet another technique for obtaining the desired VHH sequences involves suitably immunizing a transgenic mammal that is capable of expressing heavy chain antibodies (i.e., so as to raise an immune response and/or heavy chain antibodies directed against a chitinous polysaccharide), obtaining a suitable biological sample from the transgenic mammal (such as a blood sample, or any sample of B-cells), and then generating VHH sequences directed against the chitinous polysaccharide starting from the sample, using any suitable technique known per se. For example, for this purpose, the heavy chain antibody-expressing mice and the further methods and techniques described in WO 02085945 and in WO 04049794 can be used.

Accordingly, the invention encompasses methods of generating antigen-binding proteins hereof. As a non-limiting example, a method is provided for generating antigen-binding proteins specifically binding to chitinous polysaccharides, preferably to chitin, comprising:

(i) immunizing an animal with a complex mixture containing chitinous polysaccharides, and
(ii) selecting antigen-binding proteins that are binding to solubilized chitin immobilized onto a solid surface; and
(iii) screening for antigen-binding proteins specifically binding to chitin prepared on an insoluble carrier.

The screening for antigen-binding proteins, as a non-limiting example, specifically binding to a chitinous polysaccharide may for example be performed by screening a set, collection or library of cells that express heavy chain antibodies on their surface (e.g., B-cells obtained from a suitably immunized Camelid), or bacteriophages that display a fusion of genIII and VHH at their surface, by screening of a (naïve or immune) library of VHH sequences, or by screening of a (naïve or immune) library of nucleic acid sequences that encode VHH sequences, which may all be performed in a manner known per se, and which method may optionally further comprise one or more other suitable steps, such as, for example, and without limitation, a step of affinity maturation, a step of expressing the desired amino acid sequence, a step of screening for binding and/or for activity against the desired chitinous polysaccharide, a step of determining the desired amino acid sequence or nucleotide sequence, a step of introducing one or more nucleic acid substitutions, a step of formatting in a suitable multivalent and/or multispecific format, a step of screening for the desired biological and/or physiological properties (i.e., using a suitable assay known in the art), and/or any combination of one or more of such steps, in any suitable order.

A second aspect hereof is the use of an antigen-binding protein hereof to determine the presence and/or concentration of a chitinous polysaccharide in a sample.

Methods to determine the presence and/or concentration of a compound using antigen-binding proteins are known to the person skilled in the art and include, but are not limited to immunoprecipitation, fluorescent immunoassay, radio immunoassay (RIA), enzyme linked immunosorbent assay (ELISA) and magnetic immunoassay (MIA). The antigen-binding protein hereof can be labeled to facilitate the detection and/or quantification of the compound. Labeling of antigen-binding proteins is known to the person skilled in the art, and includes direct labeling and indirect labeling. In direct labeling, the antigen-binding protein itself is labeled by a directly detectable label such as, but not limited to a color label, a fluorescent label, a radioactive label or a magnetic particle. Fluorescent labels are especially useful, and include, but are not limited to fluorescein isothiocyanate (FITC) and other fluorescein derivatives, tetramethylrhodamine isothiocyanate (TRITC) and other rhodamine derivatives, R-pycoerythrin fluorescent protein (R-PE) and R-PE:cyanine-5, and allophycocyanin. Alternatively, the labeling can be carried out in an indirect way. In this case, the antigen-binding protein hereof functions can be bound to a detectable secondary compound, or is fused or bound to a tag, which on its own is not directly detectable, but can be detected by binding to a detectable secondary compound. It is obvious for the person skilled in the art that the detection can be the result of a chain of events, such as but not limited to serial binding of compounds, or activation of the label after binding.

As used herein a "sample" is a portion, piece or segment representative for a whole that one wants to analyze for the presence and/or concentration of one or more chitinous polysaccharides, preferably chitin. The sample can be a part that is withdrawn from the whole, or it can be the whole, measured at a representative point in place and/or time, as is the case for a sample measured on line by a biosensor during fermentation. As a non-limiting example, the sample can be a food sample, wherein the presence or concentration of the chitinous polysaccharide, preferably chitin, needs to be determined or changed in relation to allergenic capacity of the chitinous polysaccharide, or in relation to wanted or unwanted physical, chemical or microbiological characteristics of the chitinous polysaccharide, preferably chitin, changing the quality parameters of the food stuff, such as an altered shelf life.

In a similar way, chitin is often used as food additive, for improving the texture of the foodstuff, as thickening and stabilizing agent, and as natural flavor extender. Chitin can be used to improve nutritional quality, such as an increase in dietary fibre, to obtain a hypocholesterolemic effect, to reduce lipid adsorption and as antigastritis agent (Shahidi et al., 1999). Chitin and chitosan are also used as anti-microbials (Yalpani et al., 1992). However, the presence of chitin in food can also be due to fungal or yeast contamination, and detection of chitin has been used as a measure for such contamination, as is disclosed in WO 9217786 and in U.S. Pat. No. 5,004,699. A specific antigen-binding protein is needed to make a distinction between the possible sources and forms of chitin in food; the antigen-binding proteins hereof are specially suited for this kind of applications.

A third aspect hereof is the use of an antigen-binding protein hereof to isolate or purify a chitinous polysaccharide from a sample.

Isolation of the chitinous polysaccharide, preferably chitin, may be used to purify the chitinous polysaccharide out of a mixture, or it may be intended to remove a contaminating or otherwise undesirable chitinous polysaccharide out of a sample. Methods to use antigen-binding proteins for isolating compounds are known to the person skilled in the art and include but are not limited to immunoprecipitation and affinity chromatography. Alternatively, the antigen-binding protein hereof may be bound to a membrane, in order to be used in membrane filtration or similar techniques. Non limiting examples of the isolation and/or purification can be found in wastewater treatment.

One embodiment of the use of an antigen-binding protein hereof in purification is the purification of a fusion protein, comprising an antigen-binding protein hereof, most preferably a chitin-binding VHH. Fusion proteins are known to the person skilled in the art and consist of two or more proteins, protein parts or peptides that are joined together, either by chemical means (such as by crosslinking or by covalent binding) or by recombinant DNA methods. Immobilization and purification of recombinant fusion proteins, comprising a chitin-binding domain, on a chitin matrix is known to the person skilled in the art and has been disclosed in U.S. Pat. No. 5,258,502 and WO 03020745. Replacing or combining the chitin-binding domain by respectively with a chitin antigen-binding protein hereof has the advantage that the affinity for the matrix will be higher, and/or that the elution profile will be sharper and/or that the purification process will be more efficient.

A fourth aspect hereof is a kit for the detection of the presence and/or the determination of the concentration of a chitinous polysaccharide in a sample, comprising at least an antigen-binding protein hereof.

Apart from an antigen-binding protein hereof, which is binding to a chitinous polysaccharide, preferably to chitin, the kit may further comprise reagents needed for the labeling and/or detection and/or quantification of the antigen-binding protein. In one embodiment, the kit is used for diagnostic purposes.

A fifth aspect hereof is a biosensor for the detection of the presence and/or the determination of the concentration of a chitinous polysaccharide in a sample, comprising at least one antigen-binding protein hereof.

Preferably, the antigen-binding protein is immobilized on the sensing layer of the biosensor; the detection of the binding can be, as a non limiting example, optical, electrochemical, by quartz crystal microbalance, by magneto immune-sensors or by micromechanical cantilever-based immunosensors. The technology for the immobilization of the antigen-binding protein and for the detection of the binding between the target molecule and the antigen-binding protein is known to the person skilled in the art and has been reviewed, amongst others, by Marquette and Blum (2006), Fritz (2008) and Skottrup et al. (2008).

A sixth aspect hereof is a targeting agent, capable of binding a compound to a chitinous polysaccharide, wherein the targeting agent comprises at least one antigen-binding protein hereof.

A "targeting agent," as used herein, is a molecular structure, preferably with a polypeptide backbone, comprising at least one antigen-binding protein hereof. A targeting agent in its simplest form consists solely of one single antigen-binding protein; however, a targeting agent can comprise more than one antigen-binding protein and can be monovalent or multivalent and monospecific or multispecific, as further defined. Apart from one single or multiple antigen-binding proteins, a targeting agent can further comprise other moieties, which can be either chemically coupled or fused, whether N-terminally or C-terminally or even internally fused, to the antigen-binding protein. The other moieties include, without limitation, one or more amino acids, including labeled amino acids (e.g., fluorescently or radioactively labeled) or detectable amino acids (e.g., detectable by an antibody), one or more monosaccharides, one or more oligosaccharides, one or more polysaccharides, one or more lipids, one or more fatty acids, one or more small molecules or any combination of the foregoing. In one preferred embodiment, the other moieties function as spacers or linkers in the targeting agent.

A "compound" as used here can be any compound, preferably an active substance, including but not limited to proteins and protein complexes such as enzymes, or chemical compounds, including but not limited to agrochemical active substances, as further defined. Preferably, a compound may be comprised in or onto a carrier, preferably a microcarrier, wherein the carrier can be coupled with one or more targeting agents comprising at least one antigen-binding protein hereof. "Comprised in a carrier" as used herein means bound on or contained in by means such as but not limited to embedding, encapsulation and adsorption. Preferably, the carrier is such that the one or more compounds can be incorporated, encapsulated or included into the carrier, e.g., as a nanocapsule, microcapsule, nanosphere, micro-sphere, liposome or vesicle. Preferably the carriers are such that they have immediate or gradual or slow release characteristics, for example over several minutes, several hours, several days or several weeks. Also, the carriers may be made of materials (e.g., polymers) that rupture or slowly degrade (for example, due to prolonged exposure to high or low temperature, sunlight, high or low humidity or other environmental factors or conditions) over time (e.g., over minutes, hours, days or weeks) and so release the compound from the carrier.

The targeting agent hereof may either be a "mono-specific" targeting agent or a "multi-specific" targeting agent. By a "mono-specific" targeting agent is meant a targeting agent that comprises either a single antigen-binding protein, or that comprises two or more different antigen-binding proteins that each are directed against the same binding site. Thus, a mono-specific targeting agent is capable of binding to a single binding site, either through a single antigen-binding protein or through multiple antigen-binding proteins. By a "multi-specific" targeting agent is meant a targeting agent that comprises two or more antigen-binding proteins that are each directed against different binding sites. Thus, a "bi-specific" targeting agent is capable of binding to two different binding sites; a "tri-specific" targeting agent is capable of binding to three different binding sites; and so on for "multi-specific" targeting agents. Also, in respect of the targeting agents described herein, the term "monovalent" is used to indicate that the targeting agent comprises a single antigen-binding protein; the term "bivalent" is used to indicate that the targeting agent comprises a total of two single antigen-binding proteins; the term "trivalent" is used to indicate that the targeting agent comprises a total of three single antigen-binding proteins; and so on for "multivalent" targeting agents.

"Capable of binding a compound to a chitinous polysaccharide," as used herein, means that the binding of the antigen-binding protein, comprised in the targeting agent to the chitinous polysaccharide, is strong enough to bind, the compound, to a chitinous polysaccharide. Preferably, the compound is comprised into or onto a carrier, more preferably a microcarrier. Preferably, the targeting agent is coupled by affinity binding or by covalent binding to the compounds, even more preferably to the carrier containing the compounds. Preferably, the chitinous polysaccharide is chitin. Preferably, the chitinous polysaccharide is comprised in a solid surface or immobilized onto a solid surface.

Methods to couple the compound, preferably the plant-enhancing agent, and/or carrier to the targeting agent are known to the person skilled in the art, and include, but are not limited to covalent binding and affinity binding. An example of covalent binding is a fusion protein, wherein the targeting agent and a compound of proteinaceous nature are produced, preferably by means of recombinant protein expression, as one unity. An alternative approach to using fusion proteins is to use chemical cross-linking of residues in the targeting agent for covalent attachment to the compound, which can be a second protein or another chemical compound, using conventional coupling chemistry, for example as described by Fipula (2007) and in *Bioconjugate Techniques*, Hermanson, ed. Academic Press Inc., San Diego, Calif., USA, (2008). Amino acid residues incorporating sulphydryl groups, such as cysteine, may be covalently attached using a bispecific reagent such as succinimidyl maleimidophenylbutyrate (SMPB), for example. Alternatively, lysine groups located at the protein surface may be coupled to activated carboxyl groups on the second protein by conventional carbodiimide coupling using 1-ethyl-3-[3-dimethylaminopropyl]carbodiimide (EDC) and N-hydroxysuccinimide (NHS). The coupling between the targeting agent and the compound or carrier wherein the compound is comprised, may be direct, or a spacer or hinge molecule can be used. Examples of such spacers can be found in WO 0024884 and WO 0140310.

In one embodiment, the antigen-binding protein comprised in the targeting agent hereof is binding a chitinous polysaccharide, preferably chitin, which is comprised in or derived from an arthropod, preferably an insect, and/or the resulting targeting agent is capable of binding a compound to an arthropod, preferably an insect.

In another preferred embodiment, the antigen-binding protein comprised in the targeting agent hereof is binding a chitinous polysaccharide, preferably chitin, which is comprised in or derived from a fungus or yeast and/or the resulting targeting agent is capable of binding a compound to a fungus or a yeast.

In still another preferred embodiment, the compound is an agrochemical active substance, as further defined, with an insecticidal or an anti-fungal activity, as earlier defined.

A seventh aspect hereof is the use of a targeting agent hereof, to target a compound to a chitinous polysaccharide.

To "target" as used herein means that the compound is delivered at or near its site of action, where it can subsequently bind to a chitinous polysaccharide through the antigen-binding protein hereof which is comprised in the targeting agent. In order to be able to bind, preferably to retain, a compound, preferably an agrochemical active substance to a chitinous polysaccharide, either one single or multiple targeting agents are either fused with or attached to the compound, preferably the agrochemical active substance, either by a covalent bond, by hydrogen bonds, by dipole-dipole interactions, by weak Van der Waals forces or by any combination of the foregoing. "Attached," as used herein, means coupled to, connected to, anchored in, admixed with or covering. Preferably, the compound, more preferably, the agrochemical active substance is comprised in or onto a carrier, preferably a microcarrier. Preferably, the chitinous polysaccharide, more preferably chitin, is comprised in a solid surface or immobilized onto a solid surface.

The targeting of a compound or a combination of compounds by the targeting agent hereof can be any targeting known to the person skilled in the art, and includes, but is not limited to targeting of an enzyme to its substrate or targeting fragrance or color to chitinous polysaccharide-containing matrices. Indeed, it is known that chitin-binding domains play an essential role in the specificity of chitinases; Neeraja et al. (2010a) have demonstrated that the activity and conformational stability of chitinase can be improved by fusion to a cellulose-binding domain. A similar effect can be obtained by fusing a chitinous polysaccharide digesting catalytic domain (such as a chitinase catalytic domain) to an antigen-binding protein hereof. Other applications, such as the use of softening agents, polymeric lubricants, photoprotective agents, latexes, resins, dye fixative agents, encapsulated materials antioxidants, insecticides, anti-microbial agents, soil repelling agents or soil release agents, as well as other agents of choice, and ways and time of adding the agents to a polysaccharide-containing matrix are fully within the ordinary skill of a person skilled in the art.

In one embodiment, the compound, preferably the agrochemical active substance, is targeted to a chitinous polysaccharide, preferably to chitin, which is comprised in or derived from an arthropod, as defined above.

In another preferred embodiment, the compound, preferably the agrochemical active substance, is targeted to a chitinous polysaccharide, preferably to chitin, which is comprised in or derived from a fungus or yeast. Indeed, chitin is known to be part of the fungal cell wall, and can be used to target a compound or a combination of compounds to the fungal organism. As a non-limiting example, a chitin antigen-binding protein hereof can be coupled to an agrochemical active substance, as further defined, preferably with antifungal activity, as earlier defined, thereby delivering the agrochemical active substance to the fungus without contamination, or with a minimal contamination of the environment, eventually leading to lower residue levels of the agrochemical active substance on the crop that has been treated with the so targeted agrochemical active substance.

In still another preferred embodiment, the compound is an agrochemical active substance, as further defined, with an insecticidal or an anti-fungal activity, as earlier defined.

An eighth aspect hereof is a composition, comprising (i) at least one targeting agent hereof, and (ii) one or more compounds.

Preferably, the compounds are comprised in or onto a suitable carrier, preferably a microcarrier. Preferably, the targeting agent is coupled by affinity binding or by covalent binding to the compounds, even more preferably to the carrier containing the compounds. Preferably, the compound or combination of compounds are agrochemical active substances, as defined below.

In one embodiment, the composition is an agrochemical composition. An "agrochemical composition" as used herein means a composition for agrochemical use, as further defined, comprising at least one agrochemical active substance, as further defined, optionally with one or more additives favoring optimal dispersion, atomization, deposition, leaf wetting, distribution, retention and/or uptake of agrochemicals. As a non-limiting example such additives are diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and/or drift control agents.

"Agrochemical use," as used herein, not only includes the use of agrochemical compositions as defined above that are suitable and/or intended for use in field grown crops (e.g., agriculture), but also includes the use of agrochemical compositions that are meant for use in greenhouse grown crops (e.g., horticulture/floriculture) or hydroponic culture systems or uses in public or private green spaces (e.g., private gardens, parks, sports fields), for protecting plants or parts of plants, including but not limited to bulbs, tubers, fruits and seeds (e.g., from harmful organisms, diseases or pests), for controlling, preferably promoting or increasing, the growth of plants; and/or for promoting the yield of plants, or the parts of plants that are harvested (e.g., its fruits, flowers, seeds etc.) and even the use of agrochemical compositions that are suitable and/or intended for non-plant uses such as household uses (for example, herbicides or insecticides for household use or agents to protect fabrics or wood from damage caused by harmful organisms), or industrial uses (for example, agents to prevent fouling or to protect stored goods from damage by harmful organisms) or uses by pest control operators (for example, to control undesirable insects and rodents etc.).

"Agrochemical active substance," as used herein, means any active substance or principle that may be used for agrochemical use, as defined above. Examples of such agrochemical active substances will be clear to the skilled person and may for example include compounds that are active as insecticides (e.g., contact insecticides or systemic insecticides, including insecticides for household use), acaricides, miticides, herbicides (e.g., contact herbicides or systemic herbicides, including herbicides for household use), fungicides (e.g., contact fungicides or systemic fungicides, including fungicides for household use), nematicides (e.g., contact nematicides or systemic nematicides, including nematicides for household use) and other pesticides (for example avicides, molluscicides, piscicides) or biocides (for example, agents for killing bacteria, algae or snails); as well as fertilizers; growth regulators such as plant hormones; micro-nutrients, safeners; pheromones; repellants; baits (e.g., insect baits or snail baits); and/or active principles that are used to modulate (i.e., increase, decrease, inhibit, enhance and/or trigger) gene expression (and/or other biological or biochemical processes) in or by the targeted plant (e.g., the plant to be protected or the plant to be controlled). Agrochemical active substances include chemicals, but also nucleic acids (e.g., single stranded or double stranded RNA, as for example used in the context of RNAi technology), peptides, polypeptides, proteins (including antigen-binding proteins) and micro-organisms. "Micro-organisms" as used herein means bacteria, fungi, yeasts, viruses and the like. Examples of such agrochemical active substances will be clear to the skilled person; and for example include, without limitation: glyphosate, paraquat, metolachlor, acetochlor, mesotrione, 2,4-D,atrazine, glufosinate, sulfosate, fenoxaprop, pendimethalin, picloram, trifluralin, bromoxynil, clodinafop, fluoroxypyr, nicosulfuron, bensulfuron, imazetapyr, dicamba, imidacloprid, thiamethoxam, fipronil, chlorpyrifos, deltamethrin, lambda-cyhalotrin, endosulfan, methamidophos, carbofuran, clothianidin, cypermethrin, abamectin, diflufenican, spinosad, indoxacarb, bifenthrin, tefluthrin, azoxystrobin, thiamethoxam, tebuconazole, mancozeb, cyazofamid, fluazinam, pyraclostrobin, epoxiconazole, chlorothalonil, copper fungicides, trifloxystrobin, prothioconazole, difenoconazole, carbendazim, propiconazole, thiophanate, sulphur, boscalid and other known agrochemicals or any suitable combination(s) thereof. Other suitable agrochemicals will be clear to the skilled person based on the disclosure herein, and may for example be any commercially available agrochemical, and for example include each of the compounds listed in Phillips McDougall, AgriService November 2007 V4.0, Products Section—2006 Market, Product Index pp. 10-20. The agrochemical active substances can occur in different forms, including but not limited to, as crystals, as micro-crystals, as nano-crystals, as co-crystals, as a dust, as granules, as a powder, as tablets, as a gel, as a soluble concentrate, as an emulsion, as an emulsifiable concentrate, as a suspension, as a suspension concentrate, as a suspoemulsion, as a dispersion, as a dispersion concentrate, as a microcapsule suspension or as any other form or type of agrochemical formulation clear to those skilled in the art. Agrochemical active substances not only include active substances or principles that are ready to use, but also precursors in an inactive form, which may be activated by outside factors. As a non limiting example, the precursor can be activated by pH changes, caused by plant wounds upon insect damage, by enzymatic action caused by fungal attack, or by temperature changes or changes in humidity.

The agrochemical composition hereof may be in a liquid, semi-solid or solid form and for example be maintained as an aerosol, flowable powder, wettable powder, wettable granule, emulsifiable concentrate, suspension concentrate, microemulsion, capsule suspension, dry microcapsule, tablet or gel or be suspended, dispersed, emulsified or otherwise brought in a suitable liquid medium (such as water or another suitable aqueous, organic or oily medium) for storage or application. The agrochemical composition hereof comprises at least one, preferably more antigen-binding proteins hereof. The presence of one or more antigen-binding proteins hereof in the agrochemical composition hereof, ensures the binding of the agrochemical active substance to its site of action, such as the plant or plant part (e.g., the fruit, tuber or bulb), the plant seed or other plant-derived organic material, while sticking of the agrochemical active substance to storage containers and/or operator's equipment is avoided. Optionally, the composition further comprises one or more further components such as, but not limited to diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and/or drift control agents or the like, suitable for use in the composition hereof.

In one preferred embodiment, the agrochemical composition comprises exerts an antifungal activity, as earlier defined.

In another preferred embodiment, the agrochemical composition exerts an insecticidal activity, as earlier defined.

The invention also encompasses a method for manufacturing a composition, preferably an agrochemical composition, hereof, the method comprising (i) selecting at least one, preferably more, targeting agents hereof, and (ii) coupling the seed targeting agent(s) to a compound, preferably an agrochemical active substance, or a combination of compounds, and optionally (iii) adding further components that may be suitable for such compositions, preferably for agrochemical compositions. Preferably, the compound is comprised in a carrier, more preferably, the targeting agent(s) are coupled to the carrier, comprising the compound, preferably the agrochemical active substance.

A ninth aspect hereof is a method for improving the resistance of a plant against insect pests and/or fungal disease, the method comprising at least one application of a composition hereof to the plant or to plant parts.

If needed, the composition is dissolved, suspended and/or diluted in a suitable solution before use. The application to the plant or plant parts is carried out using any suitable or desired manual or mechanical technique for application of an agrochemical composition, including but not limited to spraying, brushing, dressing, dripping, dipping, coating, spreading, applying as small droplets, a mist or an aerosol. "Improving the resistance of a plant," as used herein, is the protection of the plant against damage or yield decrease, caused by insect pests (as defined earlier) or by fungal disease organisms (as defined earlier). Indeed, as the composition hereof has an insecticidal or a fungicidal activity, the application of the composition to the plant, may help the plant to combat damage,—and as such prevent yield losses—caused by insect pests or fungal disease organisms. "Plant part," as used herein, means any plant part whether part of an intact living or growing plant or whether isolated or separated from a plant, and even dead plant material can be envisaged. Preferably, the plant parts are selected from the group consisting of leaves, roots, fruits, cones, flowers, seeds, bulbs and tubers.

In one embodiment, the plant is a crop. "Crop" as used herein means a plant species or variety that is grown to be harvested as food, livestock fodder, fuel raw material, or for any other economic purpose. As a non-limiting example, the crops can be maize, cereals, such as wheat, rye, barley and oats, sorghum, rice, sugar beet and fodder beet, fruit, such as pome fruit (e.g., apples and pears), citrus fruit (e.g., oranges, lemons, limes, grapefruit, or mandarins), stone fruit (e.g., peaches, nectarines or plums), nuts (e.g., almonds or walnuts), soft fruit (e.g., cherries, strawberries, blackberries or raspberries), the plantain family or grapevines, leguminous crops, such as beans, lentils, peas and soya, oil crops, such as sunflower, safflower, rapeseed, canola, castor or olives, cucurbits, such as cucumbers, melons or pumpkins, fiber plants, such as cotton, flax or hemp, fuel crops, such as sugarcane, miscanthus or switchgrass, vegetables, such as potatoes, tomatoes, peppers, lettuce, spinach, onions, carrots, eggplants, asparagus or cabbage, ornamentals, such as flowers (e.g., petunias, pelargoniums, roses, tulips, lilies, or chrysanthemums), shrubs, broad-leaved trees (e.g., poplars or willows) and evergreens (e.g., conifers), grasses, such as lawn, turf or forage grass or other useful plants, such as coffee, tea, tobacco, hops, pepper, rubber or latex plants.

A tenth aspect hereof is a plant, transformed with a nucleic acid comprising a nucleic acid sequence, encoding an antigen-binding protein hereof, or any suitable fragment thereof.

In order to transform a plant with a nucleic acid comprising the nucleic acid sequence of an antigen-binding protein hereof or any suitable fragment thereof, the nucleic acid of the antigen-binding protein hereof is first cloned into a suitable expression vector, which is known by the person skilled in the art. Subsequently, the expression vector, comprising the nucleic acid sequence encoding the antigen-binding protein hereof or any suitable fragment thereof, is transformed by methods known to the person skilled in the art, including but not limited to *Agrobacterium*-mediated transformation, electroporation, microinjection or DNA- or RNA-coated particle bombardment or such other methods known to the person skilled in the art into suitable plant cells or plant tissue and eventually a plant, which incorporates the nucleic acid sequence encoding the antigen-binding protein hereof into its genome, is regenerated from the transformed plant cells or plant tissue.

In one embodiment, the plant is a crop, as defined above.

In another preferred embodiment, the plant, preferably the crop, is more resistant to damage from insect pests or fungal disease, as defined above. Indeed, as the plant is expressing an antigen-binding protein hereof, which may have an insecticidal or fungicidal activity as defined earlier, the plant may be better capable to combat damage,—and as such prevent yield losses—caused by insect pests or fungal disease organisms in comparison to a plant, not transformed with a nucleic acid sequence, encoding an antigen-binding protein hereof, or any suitable fragment thereof.

DETAILED DESCRIPTION

Examples

Example 1

Generation and Selection of VHH

Immunization of Llamas with Insect Homogenates—

Colorado Potato Beetles (*Leptinotarsa decemlineata*) were dissected, exoskeletons and wings collected, and remainders discarded. Exoskeletons and wings were separately frozen in liquid nitrogen, ground with mortar and pestle, and fine powders collected. Colorado potato beetle larvae, Pea aphids (*Acyrthosiphon pisum*), and Tobacco Budworm larvae (*Heliothis virescens*), were frozen in liquid nitrogen, ground with mortar and pestle, and fine powders collected. Collected insect materials were resuspended in PBS and total protein concentrations of suspensions were determined with Bradford protein assay. Approximate total protein concentrations were 4.2, 0.3, 4.2, 2.7, and 2.3 mg/ml for Colorado potato beetle (CPB) exoskeletons, CPB wings, Pea aphids, CPB larvae, and Tobacco Budworm larvae suspensions, respectively. Suspensions were mixed on basis of equal total protein concentration and aliquots were prepared, stored at −80° C., and suspensions were used for immunization.

Two Llamas, named Curley Sue and Jean Harlow, were immunized at weekly intervals with six intramuscular injections of mixed insect suspensions using Freund's Incomplete Adjuvant (FIA). Doses for immunizations were 125 µg total protein for days 0 and 6, and 62.5 µg total protein for days 13, 20, 27, and 34. At day 0 and at time of PBL collection at day 38, sera of llamas were collected.

Library Construction—

From each immunized llama a separate VHH library was made. RNA was isolated from peripheral blood lymphocytes, followed by cDNA synthesis using random hexamer primers and Superscript III according to the manufacturer's instructions (Invitrogen). A first PCR was performed to amplify VHH and VH DNA fragments using a forward primer mix [1:1 ratio of call001 (5'-gtcctggctgctcttctacaagg-3') and call001b (5'-cctggctgctcttctacaaggtg-3')] and reverse primer call002 (5'-ggtacgtgctgttgaactgttcc-3'). After separation of VH and VHH DNA fragments by agarose gel electrophoresis and purification of VHH DNA fragments from gel, a second PCR was performed on VHH DNA fragments to introduce appropriate restriction sites for cloning using forward primer A6E (5'-gatgtgcagctgcaggagtctg-grggagg-3' (SEQ ID NO:_) and reverse primer 38 (5'-ggactagtgcggccgctggagacggtgacctgggt-3' (SEQ ID NO:_)). The PCR fragments were digested using PstI and Eco91I restriction enzymes (Fermentas), and ligated upstream of the pIII gene in vector pMES3. The ligation products were ethanol precipitated according to standard protocols, resuspended in water, and electroporated into TG1 cells. Library sizes were at least 1E+08 independent clones for each library. Single colony PCR on randomly picked clones from the libraries was performed to assess insert percentages of the libraries. Libraries "Curley Sue" and "Jean Harlow" had ≥80% insert percentages of full-length clones. Libraries were numbered 44 and 45 for llamas "Curley Sue" and "Jean Harlow," respectively. Phage from each of the libraries were produced using VCSM13 helper phage according to standard procedures.

Phage Selections Against Chitin—

For selections against chitin, practical grade chitin (Sigma) was coated in ELISA plates (Maxisorp, Nunc). Chitin was dissolved at 10 mg/ml concentration in 85% phosphoric acid by shaking on a vortex shaker for approximately 3 hours until all particles were dissolved. Serial five-fold dilutions in PBS were prepared, precipitated chitin removed by centrifuging at 20,000 g for 5 minutes and supernatants used for coating of ELISA plates (Maxisorp, Nunc). Wells with 100 µl per well chitin solutions were coated at 4° C. overnight or over weekend. Sera of llamas Curley Sue and Jean Harlow were used to determine optimum chitin concentration for coating in a serum titer ELISA performed according to standard procedures. 25-fold and 3,125-fold diluted chitin solutions were used for selections. Wells were washed three times with PBS/0.05%-TWEEN®-20 and blocked with 5% skimmed milk in PBS (5% MPBS). Phage were suspended in 2.5% MPBS and approximately 1E+12 cfu were used for each well. After binding to the wells at room temperature for 2 hours, unbound phage were removed by extensive washing with PBS/0.05%-TWEEN®-20 and PBS. Bound phage were eluted at room temperature with 0.1 mg/ml trypsin (Sigma) in PBS for 30 minutes. Eluted phage were transferred to a polypropylene 96-well plate (Nunc) containing excess AEBSF trypsin inhibitor (Sigma). The titers of phage from target-coated wells were compared to titers of phage from blank wells to assess enrichments. Phage were amplified using fresh TG1 cells according to standard procedures. Enrichments in selection round 1 were approximately ten-fold for both libraries 44 and 45. Enrichments in selection round 2 were five- and ≥3E+03-fold for libraries 44 and 45, respectively.

Picking Single Colonies from Selection Outputs—

Fresh TG1 cells were infected with serially diluted eluted phage and plated on LB agar; 2% glucose; 100 µg/ml ampicillin. Single colonies were picked in 96-well plates containing 100 µl per well 2xTY; 10% glycerol; 2% glucose; 100 µg/ml ampicillin. Plates were incubated at 37° C. and stored at −80° C. as master plates. From selections against chitin 16 clones were picked from $1^{st}$ round selections and 30 clones were picked from $2^{nd}$ round selections for each library 44 and 45, in total 92 clones.

Example 2

Characterization of VHH

Single-Point Binding ELISA—

A single-point binding ELISA was used to identify clones binding to plant extracts. VHH-containing extracts for ELISA were prepared as follows. 96-well plates with 100 µl per well 2xTY, 2% glucose 100 µg/ml ampicillin were inoculated from the master plates and grown at 37° C. overnight. 25 µl per well of overnight culture was used to inoculate fresh 96-well deep-well plates containing 1 ml per well 2×TY; 0.1% glucose; 100 µg/ml ampicillin. After growing at 37° C. in a shaking incubator for 3 hours, IPTG was added to 1 mM final concentration and recombinant VHH were produced during an additional incubation for 4 hours. Cells were spun down by centrifugation at 3,000 g for 20 minutes, supernatants discarded, and pellets stored at −20° C. overnight. Cell pellets were thawed, briefly vortexed, and 125 µl per well of room temperature PBS was added. Cells were resuspended on an ELISA shaker platform at room temperature for 15 minutes. Plates were centrifuged at 3,000 g for 20 minutes and 100 µl per well of VHH-containing extract was transferred to polypropylene 96-well plates (Nunc) and stored at −20° C. until further use. Binding of clones from chitin selections was analyzed using ELISA plates coated with 100 µl per well of 25-fold diluted chitin, prepared similarly as for selections. After coating at 4° C. overnight and continued coating at room temperature for 1 hour on the next day, plates were washed three times with PBS/0.05%-TWEEN®-20 and blocked with 5% skimmed milk in PBS for 1.5 hours. Plates were emptied and filled with 90 µl per well 1% MPBS. Ten µl of VHH-containing extract from each clone was added to (an) antigen-coated well(s) and a blank well. VHH were allowed to bind at room temperature for 1 hour and non-binding VHH were removed by washing three times with PBS/0.05%-TWEEN®-20. Bound VHH were detected with sequential incubations with monoclonal mouse anti-histidine antibodies (Abd Serotec) in 1% MPBS/0.05%-TWEEN®-20 and rabbit anti-mouse IgG whole molecule antibodies conjugated with alkaline phosphatase (RaM/AP) (Sigma) in 1% MPBS/0.05%-TWEEN®-20. Unbound antibodies were removed by washing three times with PBS/0.05%-TWEEN®-20. The plates were washed an additional two times with PBS and 100 µl pNPP disodium hexahydrate substrate (Sigma) was added to each well. The absorbance at 405 nm was measured and the ratio of VHH bound to (a) target-coated well(s) and a non-target-coated well was calculated for each clone. From selections against chitin 28 of 92 (30%) clones had a ratio greater than 2 and these clones were analyzed further by sequencing.

Single Colony PCR and Sequencing—

Single colony PCR and sequencing was performed on ELISA positive clones as follows. Cultures from master plate wells with ELISA positive clones were diluted ten-fold in sterile water. Five µl from these diluted clones were used as template for PCR using forward primer MP57 (5'-ttatgcttccggctcgtatg-3') and reverse primer GIII (5'-ccacagacagccctcatag-3'). PCR products were sequenced by Sanger-sequencing using primer MP57 (VIB Genetic Service Facility, University of Antwerp, Belgium). From selections against chitin clones VHH 15A9, VHH 15D1, VHH 15E4, and VHH 15G2 were found. Clones VHH 15E4 and VHH 15G2 are variants of clone 15D1 with one and two amino acid substitutions, respectively.

Antibody Production and Purification—

VHH were produced in *E. coli* suppressor strain TG1 or non-suppressor strain WK6 (Fritz et al., *Nucleic Acids Research*, Volume 16 Number 14 1988) according to standard procedures. Briefly, colony streaks were made and overnight cultures from single colonies inoculated in 2×TY; 2% glucose; 100 µg/ml ampicillin. The overnight cultures were used to inoculate fresh cultures 1:100 in 2×TY; 0.1% glucose; 100 µg/ml ampicillin. After growing at 37° C. in a shaking incubator for 3 hours, IPTG was added to a 1 mM final concentration and recombinant VHH were produced during an additional incubation for 4 hours. Cells were spun down and resuspended in $\frac{1}{50}^{th}$ of the original culture volume of periplasmic extraction buffer (50 mM phosphate pH 7; 1 M NaCl; 1 mM EDTA) and incubated with head-over-head rotation at 4° C. overnight. Spheroplasts were spun down by centrifugation at 3,000 g and 4° C. for 20 minutes. Supernatants were transferred to fresh tubes and centrifuged again at 3,000 g and 4° C. for 20 minutes. Hexahistidine-tagged VHH were purified from the periplasmic extract using $\frac{1}{15}^{th}$ of the extract volume of TALON metal affinity resin (Clontech), according to the manufacturer's instructions. Purified VHH were concentrated and dialyzed to PBS using Vivaspin 5 kDa molecular weight cut-off (MWCO) devices (Sartorius Stedim), according to the manufacturer's instructions.

Example 3

VHH Binding to Chitinous Polysaccharides in ELISA

VHH Binding to Chitin in ELISA—

Titration of VHH was performed on ELISA plates (Maxisorp, Nunc) coated with chitin. Chitin was dissolved at 10 mg/ml concentration in 85% phosphoric acid by shaking on a vortex shaker for approximately 3 hours until all particles were dissolved. Dissolved chitin was diluted 25-fold in PBS and precipitated chitin removed by centrifuging at 20,000 g for 5 minutes. 100 µl per well supernatant were used for coating of ELISA plates (Maxisorp, Nunc). Plates were coated at 4° C. overnight and coating was continued at room temperature for 1 hour on the next day. Plates were washed three times with PBS/0.05%-TWEEN®-20 and blocked with 5% skimmed milk in PBS for 1 hour. Four-fold serial dilutions of purified VHH were prepared in 1% MPBS/0.05%-TWEEN®-20 in polypropylene 96-well plates. Antibody concentrations ranged from 3 µg/ml to 12 ng/ml. Antibody dilutions were transferred to the chitin-coated plates and VHH were allowed to bind for 1 hour at room temperature. Bound VHH were detected with sequential incubations with monoclonal mouse anti-histidine antibodies (Abd Serotec) and rabbit anti-mouse IgG whole molecule antibodies conjugated with alkaline phosphatase (RaM/AP) (Sigma) in 1% MPBS/0.05%-TWEEN®-20. Unbound antibodies were removed by washing three times with PBS/0.05%-TWEEN®-20 after each antibody incubation. The plates were washed an additional two times with PBS and 100 µl pNPP disodium hexahydrate substrate (Sigma) was added to each well. The absorbance at 405 nm was measured and plotted as function of antibody concentration (see Table 1).

TABLE 1

| VHH binding to chitin in ELISA: | | | | | | | |
|---|---|---|---|---|---|---|---|
| [VHH] (µg/ml) | | 3.0 | 0.75 | 0.19 | 0.047 | 0.012 | 0 |
| [VHH] (nM) | | 200 | 50 | 13 | 3.1 | 0.78 | 0 |
| Chitin | | + | + | + | + | + | + |
| | | 1 | 2 | 3 | 4 | 5 | 6 |
| VHH15A9 | A | =4.000 | 2.059 | 0.640 | 0.225 | 0.112 | 0.090 |
| VHH15D1 | B | 2.669 | 1.459 | 0.392 | 0.121 | 0.089 | 0.088 |
| Unrelated VHH | C | 0.089 | 0.086 | 0.089 | 0.089 | 0.085 | 0.088 |

Specificity of Chitin-Binding VHH in ELISA

In order to investigate the specificity of the selected chitin-binding VHH an ELISA with different coatings was used. VHH 15A9 as well as control conditions with other antibodies were tested for binding to chitin, pectin, and potato lectin. ELISA plates (Maxisorp, Nunc) were coated with 100 µl per well chitin similarly as for the titration ELISA, 100 µg/ml 20-34% esterified pectin from citrus fruits (Sigma), or potato lectin (Sigma) in PBS. Plates were coated at 4° C. overnight and coating was continued at room temperature for 1 hour on the next day. Plates were washed three times with PBS/0.05%-TWEEN®-20 and blocked with 5% skimmed milk in PBS for 1 hour. Purified VI-1H 15A9 was diluted to 3 µg/ml in 1% MPBS/0.05%-TWEEN® and added to the coated plate and VHH were allowed to bind for 1 hour at room temperature. Bound VHH were detected with sequential incubations with monoclonal mouse anti-histidine antibodies (Abd Serotec) and rabbit anti-mouse IgG whole molecule antibodies conjugated with alkaline phosphatase (RaM/AP) (Sigma) in 1% MPBS/0.05%-TWEEN®-20. Unbound antibodies were removed by washing three times with PBS/0.05%-TWEEN®-20 after each antibody incubation. The plates were washed an additional two times with PBS and 100 µl pNPP disodium hexahydrate substrate (Sigma) was added to each well. The absorbance at 405 nm was measured and binding obtained binding profile for VHH 15A9 and control antibodies compared (see Table 2). Diverse and distinct binding patterns were observed for VHH 15A9 and control antibodies. VHH 15A9 showed specific binding to chitin only.

TABLE 2

Specificity of chitin-binding VHH in ELISA

|  | VHH 15A9 specifically binding to chitin | Control condition without VHH | Control antibody binding specifically to pectin | Control antibody binding to potato lectin and pectin |
| --- | --- | --- | --- | --- |
| Chitin coating | 0.846 | 0.110 | 0.115 | 0.114 |
| Pectin coating | 0.118 | 0.114 | 3.171 | 0.409 |
| Potato lectin coating | 0.114 | 0.112 | 0.118 | 3.878 |
| No coating control condition | 0.109 | 0.111 | 0.111 | 0.116 |

Example 4

Binding of VHH to Chitin Beads

Binding of VHH to Chitin Beads—

Anti-chitin VHH were analyzed for binding to paramagnetic chitin beads (New England Biolabs). These beads are formed through emulsion chemistry starting with low molecular weight chitosan and encapsulation of magnetite particles during bead formation. Once the beads are formed they are acetylated to ensure that they are chitin beads. Beads were equilibrated by five washes with 500 mM NaCl/20 mM Tris-HCl/1 mM EDTA/0.1%-TWEEN®-20 using a Dynamag spin magnet (Invitrogen) and removing supernatants by pipetting. Equilibrated beads were dispensed and incubated with 5 µg/ml histidine-tagged anti-chitin VHH in 1% BSA/PBS with head-over-head rotation at 4° C. for 2 hours. Control conditions included incubations with unrelated VHH in 1% BSA/PBS or with 1% BSA/PBS alone. Non-bound VHH were washed away by five washes with PBS and bound VHH were detected by consecutive incubations with monoclonal mouse anti-histidine antibodies (Abd Serotec) and rabbit anti-mouse IgG whole molecule antibodies conjugated with alkaline phosphatase (RaM/AP) (Sigma). Antibodies were diluted in 1% BSA/PBS and incubated at room temperature for 1 hour. Non-bound antibodies were removed by washing five times with PBS in between different incubations. After final washes and removal of supernatant pNPP disodium hexahydrate substrate (Sigma) was added to each condition and incubated for 10 minutes. Substrates were transferred to an optical plate and the absorbance at 405 nm was measured. Measured absorbance was 4.0 (saturated), 4.0 (saturated), 3.8, 4.0 (saturated), 0.23, and 0.20 for VHH 15D1, VHH 15E4, VHH 15G2, VHH 15A9, unrelated VHH, and incubation without VHH, respectively. These data show that after selecting and performing primary screens on practical grade chitin VHH 15D1, VHH 15E4, VHH 15G2, and VHH 15A9 are truly binding chitin.

Example 5

Binding of VHH-Coupled Microcapsules to Immobilized Chitinous Polysaccharide

With the objective to generate VHH-functionalized polyurea microcapsules, VHH were coupled to microcapsules with a core of 1.5% Uvitex OB (Ciba) in benzyl benzoate and a shell with incorporated lysine to surface-expose carboxyl groups. A core of 1.5% Uvitex OB in benzyl benzoate was used for fluorescent visualization of microcapsules. After production of microcapsules, microcapsules were washed with water and stored as capsule suspensions in water. Before coupling of VHH, microcapsules were washed with MES/NaCl buffer (0.1 M MES/0.5 M NaCl pH 6) using a 96-well deep-well filtration plate (Millipore) and vacuum manifold (Millipore). A panel of VHH was dialyzed to MES/NaCl buffer and added to a final concentration of 10-70 µM and incubated with the microcapsules for 15-30 minutes. 1-Ethyl-3-[3-dimethylaminopropyl]carbodiimide Hydrochloride (EDC) (Pierce) was dissolved in MES/NaCl buffer and promptly added to a final concentration of 50 mM. VHH were coupled by incubation with continuous mixing at room temperature for 2 hours. The coupling reactions were stopped by adding glycine or Tris-buffer pH 7.5 to a final concentration of 100 mM and incubation at room temperature for 30 minutes. Non-bound VHH were collected using the filtration plate setup using a deep-well collector plate. Microcapsules were washed three times with PBS and resuspended in PBS and stored at 4° C. until use.

An ELISA-like assay setup was used to evaluate the interaction of VHH-coupled microcapsules to chitinous polysaccharides-containing surfaces. Wells of a high bind half area microplate (Greiner Bio-One) were coated with chitin. Coating with chitin was performed as before for the titration and specificity ELISAs. 100 µg/ml potato lectin in PBS was coated as control condition. The microplate was washed three times with PBS with 0.05%-TWEEN®-20 and blocked with 5% skimmed milk in PBS for 2 hours. VHH-coupled microcapsules containing a fluorescent tracer were diluted to appropriate density in 1% skimmed milk in PBS with 0.05%-TWEEN®-20. Microcapsules were added in serial dilution to the chitin-coated or control wells and allowed to bind for 1 hour. Unbound microcapsules were removed by washing five times with PBS with 0.05%-TWEEN®-20. The bottoms of ELISA plate wells were analyzed for fluorescence using a multimode microplate reader (Tecan) for bound microcapsules (see Table 3).

TABLE 3

Use of VHH for binding of microcapsules to immobilized chitinous polysaccharides. A bottom scan was performed to investigate bound fluorescent tracer microcapsules to chitin or control antigen-coated surfaces.

| | Microcapsule amount | Fluorescent tracer microcapsules with VHH 15A9 | Blank microcapsules without VHH |
|---|---|---|---|
| Chitin coating | 100% | 10621 | 2101 |
| Chitin coating | 20% | 985 | 356 |
| Chitin coating | 4% | 262 | 142 |
| Potato lectin coating | 100% | 837 | 3206 |
| Potato lectin coating | 20% | 581 | 645 |
| Potato lectin coating | 4% | 157 | 212 |

Example 5

Binding of Microcapsules, Coupled with VHH, to Chitin Beads

Binding of VHH-coupled microcapsules to chitin magnetic beads was investigated with paramagnetic chitin beads (New England Biolabs). Beads were equilibrated by five washes with 500 mM NaCl/20 mM Tris-HCl/1 mM EDTA/ 0.1%-TWEEN®-20 using a Dynamag spin magnet (Invitrogen) and removing supernatants by pipetting. 1 mg quantities of beads were dispensed and the approximate concentration of beads was calculated from the diameter of the beads (ø 50-70 µm). Chitin beads were incubated with a 100-fold excess of microcapsules (ø 10 µm) over the number of chitin beads in 1% BSA in PBS and binding was allowed for 1 hour with head-over-head rotation at room temperature. Control conditions included incubations with blank microcapsules to which no VHH had been coupled. Five washes were performed with PBS using head-over-head rotation for each wash and using the Dynamag spin magnet to collect the beads in between each wash step. Beads with bound microcapsules were finally resuspended in a small volume and transferred to an 18-well µ slide (Ibidi) and analyzed for bound microcapsules on a macrozoom microscope system (Nikon). Microcapsules were counted using Volocity image analysis software (Perkin Elmer). A DAPI filter was used to visualize Uvitex microcapsules. 2.2E+03 microcapsules were found on 1 mg chitin beads with VHH 15D1-coupled microcapsules. Only 7.1E+02 microcapsules were found on 1 mg chitin beads with blank microcapsules to which no VHH had been coupled. Advantageous binding to chitin magnetic beads was obtained with microcapsules with coupled VHH binding to chitin.

REFERENCES

Altschul, S. F., Madden, T. L., Schäffer, A. A., Zhang, J., Zhang, Z., Miller, W. and Lipman, D. J. (1997). Gapped BLAST and PSI-BLAST: a new generation of protein database search programs, Nucleic Acids Res. 25:3389-3402.

Bona, C. (1993). Molecular characteristics of anti-polysaccharide antibodies. Springer Semin. Immunopathol 15, 103-118.

Boot, R. G., Renkema, G. H., Strijland, A., van Zonneveld, A. J. and Aerts, J. M. F. G. (1995). Cloning of a cDNA encoding chitotriosidase, a human chitinase produced by macrophages. J. Biol. Chem. 44, 26252-26256.

Cisar, J., Kabat, E. A., Dorner, M. M. and Liao, J. (1975) binding properties of immunoglobulin combining sites specific for terminal or nonterminal antigenic determinants in dextran. J. Exp. Med. 142, 435-459.

Daley, L. P., Kutzler, M. A., Bennett, B. W., Smith, M. C., Glaser, A. L. and Appleton, J. A. (2010). Effector functions of camelid heavy chain antibodies in immunity of west Nile virus. Clin. Vacc. Immunol. 17, 239-246.

De Simone, E. A., Saccodossi, N., Ferrari, A. and Leoni, J. (2008). Development of ELISAs for the measurement of IgM and IgG subclasses in sera from llamas (*Lama glama*) ans assessment of the humoral immune response against different antigens. Vet. Immunol. Immunopathol. 126, 64-73.

Dolk, E., van der Vaart, M., Hulsik, D. L., Vriend, G., de Haard, H., Spinelli, S., Cambillau, C., Frenken, L. And Verrips, T. (2005). Isolation of Llama antibody fragments for prevention of Dandruff by phage display in shampoo. Appl. Environ. Microbiol. 71, 442-450.

Dotan, I., Fiszhman, S., Dgani, Y., Schwartz, M., Karban, A., Lerner, A., Weishauss, O., Spector, L., Shtevi, A., Altstock, R. T., Dotan, N. and Halpern, Z. (2006). Antibodies against laminaribioside and chitobioside are novel serological markers in Crohn's disease. Gastroentrology 131, 366-378.

Ferrandon, S., Sterzenbach, T., Mersha, F. B. and Xu, M. Q. (2003). A single surface tryptophan in the chitin-binding domain from *Bacillus circulans* chitinase A1 plays a pivotal role in binding chitin and can be modified to create an elutable affinity tag. Biochim. Biophys. Acta 1621, 31-40.

Fipula, D. (2007). Antibody engineering and modification techniques. Biomolecular Engineering 24, 201-205.

Folders, J., Tommassen, J., van Loon, L. And Bitter, W. (2000). Identification of a chitin-binding protein secreted by *Pseudomonas aeruginosa*. J. Bacteriol. 182, 1257-1263.

Fritz, J. (2008). Cantilever biosensors. Analyst, 133, 855-863.

Guillen, D., Sanchez, S and Rodriguez-Sanoja, R. (2010). Carbohydrate-binding domains: multiplicity of biological roles. Appl. Microbiol. Biotechnol. 85, 1241-1249.

Hamers-Casterman, C., Atarhouch, T., Muyldermans, S., Robinson, G., Hamers, C., Bajyana Songa E., Bendahman, N. and Hamers, R. (1993) Naturally occurring antibodies devoid of light chains. Nature, 363, 446-448.

Iseli, B., Boller, T and Neuhaus, J. M. (1993). The N-terminal cysteine rich domain of tobacco class I chitinase is essential for chitin binding but not for catalytic or antifungal activity. Plant Physiol. 103, 221-226

Itoh, Y., Kawase, T., Nikaidu, N., Fukada, H., Mitsumi, M. Watanabe, T. and Itoh, Y. (2002) Functional analysis of the chitin-binding domain of a family 19 chitinase from *streptomyces griseus* HUT6037: substrate binding affinity and cis-dominant increase of antifungal function. Biosci. Biotechnol. Biochem. 66, 1084-1092.

Joshi, M. C., Sharma, A., Kant, S., Birah., A., Gupta, G. P., Khan, S. R., Bhatnagar, R. And Banjeree, N. (2008). An insecticidal GroEL protein with chitin-binding activity from *Xenorhabdus nematophila*. J. Bill. Chem. 283, 28287-28296.

Mammen, M., Choi, S. K. and Whitesides, G. M. (1998) Polyvalent interaction in Biological systems: implications for design and use of multivalent ligands and inhibitors. Angew. Chem. Int. Ed., 37, 2754-2794.

Marquette C. A., and Blum, L. C. (2006). State of the art and recent advances in immunoanalytical system. Biosensors and Bioelectronics, 21, 1424-1433.

Martin, R., Hild, S., Walther, P., Ploss, K, Boland, W. And Tomaschko, K. H. (2007). Granula&r chitin in the epidermis of nudibranch molluscs. Biol. Bull. 231, 307-315.

Muyldermans, S., Cambillau, C. And Wyns, L. (2001) Recognition of antigens by single domain antibody fragments: the superfluous luxury of paired domains. Trends Biochem. Sci. 26, 230-235.

Nakamura, A., Furuta, H., Maeda, H., Takao, T. and Nagamatsu, Y. (2002) Structural studies by stepwise enzymatic degradation of the main backbone of soybean soluble polysaccharides consisting of galacturonan and rhamnogalacturonan. Biosci. Biotechnol. Biochem. 66, 1301-1313.

Neeraja, C., Moersbacher, B., and Podile, A. R. (2010a). Fusion of cellulose-binding domain to the catalytic domain improves the activity and conformational stability of chitinase in *Bacillus lichenformis* DSM13. Bioresource technology 101, 3635-3641.

Neeraja, C., Subramanyam, R., Moerschbacher, B. M. and podile, A. R. (2010b). Swapping the chitin-binding domain in *Bacillus* chitinases improves the substrate-binding affinity and conformational stability. Mol. Biosys. 6, 1492-1502.

Saerens, D., Pellis, M., Loris, R., Pardon, E., Dumoulin, M., Matagne, A., Wyns, L., Muyldermans, S. and Conrath, K. (2005). Identification of a universal VHH framework to graft non-canonical antigen-binding loops of camel single-domain antibodies. J. Mol. Biol. 352, 597-607.

Sales, M. P., Pimenta, P. P., Paes, N. S., Grossi-de-Sa, M. F. and Xavier-Filho, J. (2001). Vicilins (7S storage globulins) of cowpea (*Vigna unguiculata*) seeds bind to chitinous structures of the midgut of *Callosobruchus maculates* (Coleoptera: Bruchidae) larvae. Braz. J. Med. Biol. Res. 34, 27-34.

Sendid, B., Dotan, N., Nseir, S., Savaux, C., Vandewalle, P., Standart, A., Zeimech, F., Guery, B. P., Dukler, A., Colombel, J. F. and Poulain, D., (2008) Antibodies against glucan, chitin and *Saccharomyces cerevisiae* mannan an new biomarkers of *candida albicans* infection that complements tests based on *C. albicans* mannan. Clin. Vacc. Immunol. 15, 1868-1877.

Seow, C. H., Stempak, J. M., Xu, W., Lan, H., Griffiths, A. M., Greenberg, G. R., Steinhart, A. H., Dotan, N. and Silverberg, M. S. (2008). Two novel polysaccharide antibodies (anti-lainarin and anti-chitin) predict an aggressive Crohn's disease phenotype and improve differentiation between Crohn's disease and ulcerative colitis. Gastroentrology, 134, A-53 (abstract 391).

Seow, C. H., Stempak, J. M., Xu, W., Lan, H., Griffiths, A. M., Greenberg, G. R., Steinhart, A. H., Dotan, N. and Silverberg, M. S. (2009). Novel anti-glycan antibodies related to inflammatory bowel diseas diagnosis and phenotype. Am. J. Gastroenterology 104, 1426-1434.

Shahidi F., Arachchi, J. K. V and Jeon Y. J. (1999). Food applications of chitin and chitosans. Trends in food science and technology, 10, 37-51.

Skottrup, P. D., Nicolaisen, M. and Justesen, A. F. (2008). Towards on-site pathogen detection using antibody-based sensors. Biosensors and Bioelectronics, 24, 339-348.

Suetake, T., Tsuda, S., Kawabata, S., Miura, K., Iwanga, S., Hikichi, K., Nitta, K. and Kawano, K. (2000). Chitin-binding proteins in ivertebrates and plants comprise a common chitin-binding structural motif. J. Biol. Chem., 275, 17929-17932.

Van der Linden, R. H. J., Frenken, L. G. J., de Geus, B., Harmsen, M. M., Ruuls, R. C., Stok, W., de Ron, L., Wilson, S., Davis, P. And Verrips, C. TR. (1999). Comparison of physical chemical properties of llama $V_{HH}$ antibody fragments and mouse monoclonal antibodies. Biochim. Biophys. Acta, 1431, 37-46.

Xu, M. Q., Paulus, H. and Chong, S. (2000). Fusions to self splicing inteins for protein purification. Methods enzymology 326, 376-418.

Yalpani, M., Johnson, F. and Robinson, L. E. (1992). Antimicrobial activity of some chitosan derivatives. In *Advances in chitin and chitosan*, Brine, C. J., Sanford, P. A. and Zikakis J. P. eds., Elsevier applied Science, London, UK, pp 543-555.

---

The invention claimed is:

1. A single chain antigen-binding protein comprising a VHH sequence, wherein the VHH sequence is able to bind a chitinous polysaccharide.

2. The antigen-binding protein of claim 1, wherein said antigen-binding protein is a monoclonal antigen-binding protein.

3. The antigen-binding protein of claim 1, wherein said chitinous polysaccharide is chitin.

4. The antigen-binding protein of claim 1, wherein said chitinous polysaccharide is comprised in or derived from an arthropod.

5. The antigen-binding protein of claim 1, wherein said chitinous polysaccharide is comprised in or derived from a fungus or a yeast.

6. The antigen-binding protein of claim 1, wherein said antigen-binding protein has an insecticidal activity.

7. The antigen-binding protein of claim 1, wherein said antigen-binding protein has an antifungal activity.

8. The antigen-binding protein of claim 1, wherein said VHH comprises a sequence selected from the group consisting of SEQ ID NO:1 through SEQ ID NO:4.

9. A method of determining the presence and/or concentration of a chitinous polysaccharide in a sample, the method comprising:
utilizing the antigen-binding protein of claim 1 to determine the presence and/or concentration of the chitinous polysaccharide in the sample.

10. A method of isolating or purifying a chitinous polysaccharide from a sample, the method comprising:
utilizing the antigen-binding protein of claim 1 to isolate or to purify the chitinous polysaccharide from the sample.

11. A method for detecting and/or determining the concentration of one or more chitinous polysaccharides, the method comprising:
utilizing at least one antigen-binding protein of claim 1.

12. A targeting agent able to bind a compound to a chitinous polysaccharide, wherein said targeting agent comprises at least one antigen-binding protein of claim 1.

13. A process for producing a transgenic plant, the method comprising:
transforming the plant with a nucleic acid molecule comprising a nucleotide encoding the antigen-binding protein of claim 1.

14. The antigen-binding protein of claim 1, further comprising a compound bonded thereto.

15. The antigen-binding protein of claim 14, wherein the compound is an agrochemical composition.

16. The antigen-binding protein of claim 15, wherein the compound has insecticidal activity.

17. The antigen-binding protein of claim 15, wherein the compound has antifungal activity.

18. A method for improving the resistance of a plant against insect pests and/or fungal disease, the method comprising:
applying at least once the antigen-binding protein of claim 1 to the plant or to plant parts in an amount that improves the resistance of a plant against insect pests and/or fungal disease.

19. A method of delivering a compound to a chitinous polysaccharide, the method comprising:
utilizing the antigen-binding protein of claim 14 to deliver the compound to the chitinous polysaccharide.

20. The method according to claim 19, wherein the chitinous polysaccharide is contained in an insect.

21. The method according to claim 20, wherein the chitinous polysaccharide is contained in a fungus.

* * * * *